US012631535B2

(12) United States Patent
Zanotto et al.

(10) Patent No.: US 12,631,535 B2
(45) Date of Patent: May 19, 2026

(54) OUTSOLE-EMBEDDED OPTOELECTRONIC SENSOR TO MEASURE SHEAR GROUND REACTION FORCES DURING LOCOMOTION

(71) Applicant: THE TRUSTEES OF THE STEVENS INSTITUTE OF TECHNOLOGY, Hoboken, NJ (US)

(72) Inventors: Damiano Zanotto, Jersey City, NJ (US); Ton Duong, Glen Ridge, NJ (US)

(73) Assignee: The Trustees of the Stevens Institute of Technology, Hoboken, NJ (US)

( * ) Notice: Subject to any disclaimer, the term of this patent is extended or adjusted under 35 U.S.C. 154(b) by 603 days.

(21) Appl. No.: 17/928,229

(22) PCT Filed: May 28, 2021

(86) PCT No.: PCT/US2021/035004
§ 371 (c)(1),
(2) Date: Nov. 28, 2022

(87) PCT Pub. No.: WO2021/243292
PCT Pub. Date: Dec. 2, 2021

(65) Prior Publication Data
US 2023/0221229 A1     Jul. 13, 2023

Related U.S. Application Data

(60) Provisional application No. 63/031,424, filed on May 28, 2020.

(51) Int. Cl.
*G01N 3/24* (2006.01)
*A61B 5/00* (2006.01)
*A61B 5/11* (2006.01)

(52) U.S. Cl.
CPC ................ *G01N 3/24* (2013.01); *A61B 5/112* (2013.01); *A61B 5/6807* (2013.01); *G01N 2203/0025* (2013.01)

(58) Field of Classification Search
CPC .. G01N 3/24; G01N 2203/0025; A61B 5/112; A61B 5/6807; A61B 5/1036; G01D 5/34; G01L 5/166
See application file for complete search history.

(56) References Cited

U.S. PATENT DOCUMENTS 3,952,880 A * 4/1976 Hill ...................... B25J 19/021
901/29
6,145,389 A    11/2000 Ebeling et al.
(Continued)

FOREIGN PATENT DOCUMENTS

| DE | 102015007106 | 12/2016 |
| WO | 2017058913 | 4/2017 |
| WO | 2019/103700 A1 | 5/2019 |

OTHER PUBLICATIONS ("Development of a Bendable Outsole Biaxial Ground Reaction Force Measurement System" by Park et al. (Year: 2019).*
(Continued)

*Primary Examiner* — Xin Y Zhong
(74) *Attorney, Agent, or Firm* — Clark Hill PLC; Ralph W. Selitto; John K. Kim

(57) ABSTRACT

A sensor apparatus for footwear includes at least one pair of light sources and at least one pair of light receivers, each light receiver being positioned and configured to receive light emitted from a respective one of the light sources. A pair of movable curtains functions to adjust the amount of light received by the pair of light receivers. The curtains are movable conjointly such that the amount of light received by one of the light receivers is inversely proportional to the
(Continued)

amount of light received by the other light receiver. (FIG. 1B).

26 Claims, 13 Drawing Sheets

(56) References Cited

U.S. PATENT DOCUMENTS

| | | |
|---|---|---|
| 7,717,826 B2 | 5/2010 | Cox et al. |
| 8,109,890 B2 | 2/2012 | Kamiar et al. |
| 9,179,862 B2 | 11/2015 | Stergiou et al. |
| 9,198,821 B2 | 12/2015 | Unluhisarcikli et al. |
| 9,307,932 B2 | 4/2016 | Mariani et al. |
| 9,470,705 B2 | 10/2016 | Statham |
| 9,681,826 B2 | 6/2017 | Dunias et al. |
| 9,687,712 B2 | 6/2017 | Statham et al. |
| 9,713,439 B1 | 7/2017 | Wu et al. |
| 2006/0282017 A1 | 12/2006 | Avni |
| 2007/0203435 A1 | 8/2007 | Novak |
| 2009/0135001 A1 | 5/2009 | Yuk |
| 2009/0240171 A1 | 9/2009 | Morris Bamberg |
| 2010/0004566 A1 | 1/2010 | Son et al. |
| 2011/0054358 A1 | 3/2011 | Kim |
| 2011/0054359 A1 | 3/2011 | Sazonov et al. |
| 2012/0116550 A1 | 5/2012 | Hoffman et al. |
| 2013/0041617 A1 | 2/2013 | Pease |
| 2013/0096466 A1 | 4/2013 | Sarrafzadeh |
| 2013/0192071 A1 | 8/2013 | Esposito et al. |
| 2015/0182843 A1 | 7/2015 | Esposito et al. |
| 2016/0331557 A1 | 11/2016 | Tong et al. |
| 2017/0055880 A1 | 3/2017 | Agrawal et al. |
| 2017/0189752 A1 | 7/2017 | Mohrman et al. |

OTHER PUBLICATIONS

Hannink et al., "Mobile Stride Length Estimation With Deep Convolutional Neural Networks," IEEE Journal of Biomedical and Health Informatics, vol. 22, No. 2, Mar. 2018, 354-362.

Zihajehzadeh et al., "Experimental Evaluation of Regression Model-Based Walking Speed Estimation Using Lower Body-Mounted IMU," 2016 38th Annual International Conference of the IEEE Engineering in Medicine and Biology Society (EMBC), 2016, 243-246.

Kim Ji-Chul et al, "Note: A compact three-axis optical force/torque sensor using photo-interrupters", Review of Scientific Instruments 84, 126109 (2013), Dec. 31, 2013 (Dec. 31, 2013), XP055837275.

Crea et al., "A Wireless Flexible Sensorized Insole for Gait Analysis," Sensors, vol. 14, Jan. 9, 2014, 1073-1093.

Hoang et al., "Gait Classification for Parkinson's Disease Using Stacked 2D and 1D Convolutional Neural Network," 2019 International Conference on Advanced Technologies for Communications (ATC), 2019, 44-49.

Lai et al., "Computational Intelligence in Gait Research: A Perspective on Current Applications and Future Challenges," IEE Transactions on Information Technology in Biomedicine, vol. 13, No. 5, Sep. 2009, 687-702.

Lugade et al., "Center of mass and base of support interaction during gait," Gait & Posture vol. 33, 2011, 406-411.

PCT International Search Report and Written Opinion for PCT/US2021/035004, "An Outsole-Embedded Optoelectronic Sensor to Measure Shear Ground Reaction Forces During Locomotion," mailed on Sep. 13, 2021, 13 pages.

PCT International Search Report and Written Opinion for PCT/US2022/027323, entitled "Accurate Ambulatory Gait Analysis with Wearable Sensors Using Transductive Learning Inference Models," mailed on Jul. 27, 2002, 15 pages.

Zhang et al., "Robot-Assisted and Wearable Sensor-Mediated Autonomous Gait Analysis," 2020 IEEE International Conference on Robotics and Automation, May 31-Aug. 31, 2020, Paris, France, 6795-6802.

Zhang et al., "Transductive Learning Models for Accurate Ambulatory Gait Analysis in Elderly Residents of Assisted Living Facilities," IEEE Transactions on Neural Systems and Rehabilitation Engineering, vol. 30, 2022, 124-134.

Zhang et al., "Estimating CoP Trajectories and Kinematic Gait Parameters in Walking and Running Using Instrumented Insoles," IEEE Robotics and Automation Letters, vol. 2, No. 4, Oct. 2017, 2159-2165.

Zhang et al., "Regression Models for Estimating Kinematic Gait Parameters with Instrumented Footwear," 2018 7th IEEE International Conference on Biomedical Robotics and Biomechatronics (Biorob), Enschede, The Netherlands, Aug. 26-29, 2018, 1169-1174.

Hannink et al., "Mobile Stride Length Estimation with Deep Convolutional Neural Networks," 2017 IEEE Journal of Biomedical and Health Informatics, vol. 22, No. 2, Mar. 9, 2017, 354-362.

Xing et al., "Pedestrian Stride Length Estimation from IMU Measurements and ANN Based Algorithm," Journal of Sensors, vol. 2017, Article ID 6091261, 2017, 1-11.

Wang et al., "Pedestrian Stride-Length Estimation Based on LSTIM and Denoising Autoencoders," Sensors, vol. 19, No. 840, 2019, 1-23.

Zrenner et al., "Comparison of Different Algorithms for Calculating Velocity and Stride Length in Running Using Inertial Measurement Units," Sensors, vol. 18, No. 4194, 2018, 1-22.

McGinnis et al., "A machine learning approach for gait speed estimation using skin-mounted wearable sensors: From healthy controls to individuals with multiple sclerosis," PLOS One, vol. 12, No. 6, e0178366, Jun. 1, 2017, 1-11.

Gibson et al., "CyberCoach: A wearable Biofeedback System for Runners," 2022 9th IEEE RAS/EMBS International Conference for Biomedical Robotics and Biomechatronics (BioRob), Aug. 21-24, 2022, 1-6.

Wouda et al., "Estimation of Vertical Ground Reaction Forces and Sagittal Knee Kinematics During Running Using Three Inertial Sensors," Frontiers in Physiology, vol. 9, Article 218, Mar. 22, 2018, 1-14.

Duda et al., "Pattern Classification," John Wiley & Sons, 2012.

Office Action for U.S. Appl. No. 17/931,527, entitled "Wireless and Retrofittable In-Shoe System for Real-Time Estimation of Kinematic and Kinetic Gait Parameters," 22 pages, issued Jul. 25, 2025.

* cited by examiner

FIG. 3D

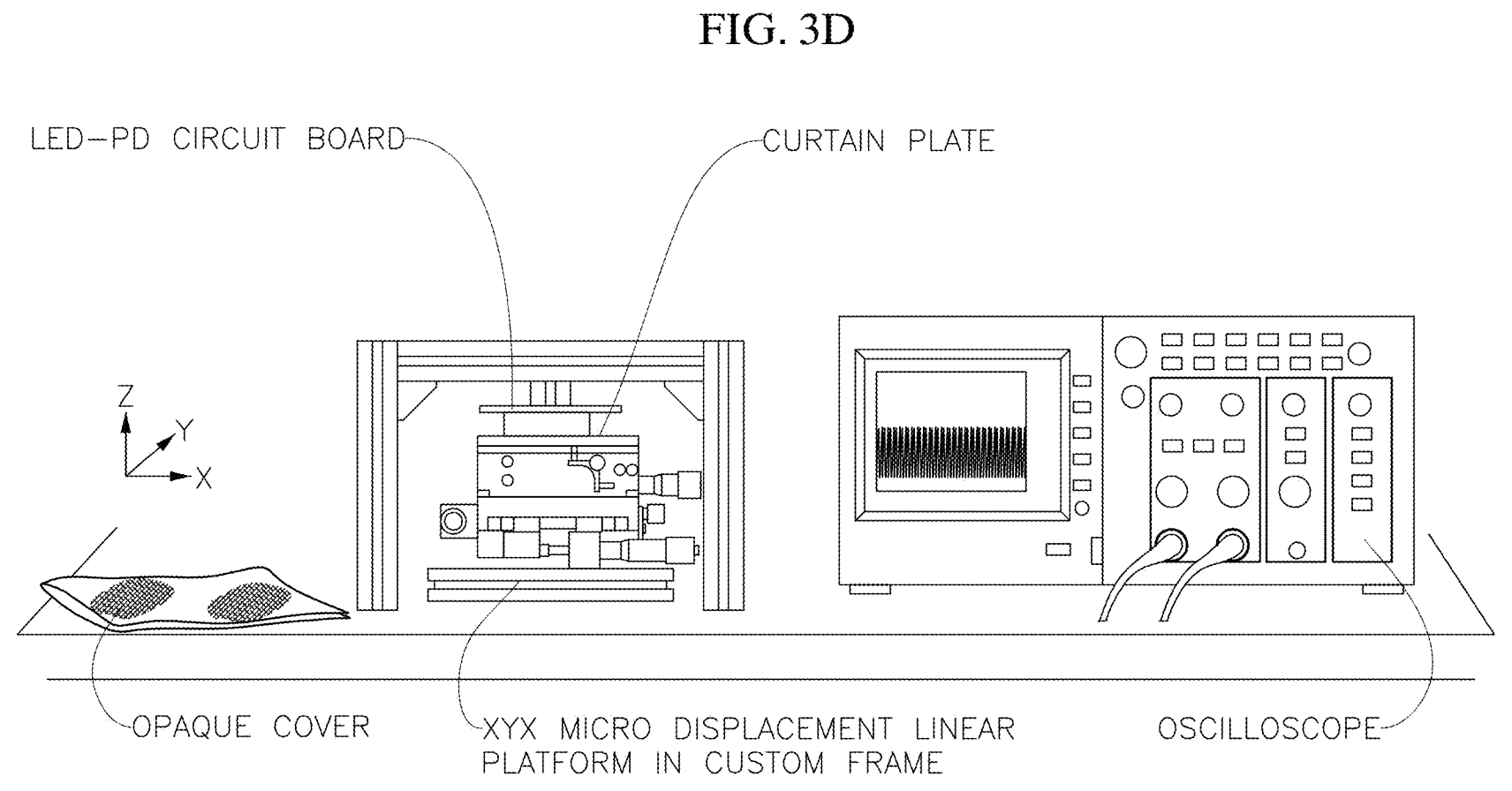

CURTAIN PLATE

LED–PD CIRCUIT BOARD

OSCILLOSCOPE

XYX MICRO DISPLACEMENT LINEAR PLATFORM IN CUSTOM FRAME

OPAQUE COVER

Z

Y

X

OUTSOLE-EMBEDDED OPTOELECTRONIC SENSOR TO MEASURE SHEAR GROUND REACTION FORCES DURING LOCOMOTION

CROSS-REFERENCE TO RELATED APPLICATIONS

This application is a U.S. National Phase entry under 35 U.S.C. 371 and claims priority to International Patent Application No. PCT/US2021/035004 filed on May 28, 2021, which claims priority to U.S. Provisional Patent Application No. 63/031,424 filed May 28, 2020, the entire disclosure of each of said applications being incorporated herein by reference.

STATEMENT REGARDING FEDERALLY SPONSORED RESEARCH

This invention was made with government support under Contract H98230-08-D-0171, Project #SOF-19, awarded by the U.S. Department of Defense through the Systems Engineering Research Center (SERC). The government has certain rights in the invention.

FIELD OF THE INVENTION

The present disclosure relates generally to sensors for measuring ground reaction forces during locomotion, and to methods, systems and apparatus (such as shoes) utilizing same.

BACKGROUND OF THE INVENTION

Wearable robotics has been gaining a significant role in many crucial fields, such as healthcare and military. Safe human-robot physical interaction (pHRI) is a crucial design priority for any wearable robot. Low-level impedance control is typically applied to guarantee safe pHRI. In these controllers, on-board force and torque sensors are used in feedback loops to guarantee proper tracking of the desired interaction forces. More recently, on-line estimation of ground reaction forces ("GRFs") has been used in lower-extremity exoskeletons to estimate the wearer's net joint moments and inform assistive controllers. Compared with electromyography-based methods, GRF-based methods have the potential to improve usability and user comfort.

The conventional method to measure 3D GRFs in gait laboratories relies on force plates or instrumented treadmills that operate based on strain gauges. However, these specialized devices are expensive and bulky, which make them unsuitable for measuring forces in unconstrained environments. While a number of pressure-sensitive instrumented footwear are available for the estimation of vertical GRF in out-of-the-lab conditions, accurately measuring anteroposterior and mediolateral GRF in real-life conditions still remains a challenging task.

Various types of miniature shear force sensors have been developed in recent years. The most common type consists of custom piezoresistive sensors, wherein the change in electrical resistance is directly proportional to the strain caused by the applied force. Fabricated microscale piezoresistive sensors that can measure shear stress on contact surfaces have been proposed. Triaxial tactile force sensors, which are capable of measuring normal and shear force using a microscale piezoresistive beams structure, have also been proposed.

Another type of shear force sensor is the capacitive pressure sensor. In this type of sensor, the change of electrical capacitance depends on the perpendicular surface areas and on the distance between two parallel conductive plates.

Electrical induction can also be used to measure normal and shear forces. For example, it has been proposed to monitor inductance changes across three planar sensing coils.

Optoelectronic force sensors are also known. Compared to other sensor types, optoelectronic sensors are less affected by electromagnetic interferences, which make them a robust option in harsh environments. For example, shear and plantar pressure sensors based on fiberoptic bend loss have been proposed. The design of this sensor type is often constructed of multiple optical fiber mesh layers wherein the loss of light passing through each fiber depends on the deformation of the encapsulating material. By way of further example, an ultrathin biaxial shear sensor, which is based on the optical coupling between vertical cavity surface emitting laser (VC-SEL) diodes and photodiodes (PDs) embedded in two parallel surfaces, has been proposed. Another proposal involves an insole instrumented with 64 pressure sensitive elements, each of which converts the applied normal force to output voltage based on the amount of light passing from a light-emitting diode (LED) to a PD through an opaque screen which gradually closes following the deformation of the silicon bulk. Yet another proposal involves a multiaxial optoelectronic force sensor that measures the reflected light paths from a center VCSEL to the coplanar surrounding PDs based on the deformation of the trapezoidal structure. It has also been proposed to provide an optically based silicone insole with photomicrosensors and reflective surfaces adapted to measure 3D GRFs.

Wearable GRF sensors can be mounted externally or internally to the footwear. With internal, or "in-shoe", mounting, the sensing elements are often embedded in the insoles or socks, where they can be used to measure footsole interaction forces and center of pressure trajectories. Because of the limited space in the footwear, the design priorities for "in shoe" implementations are wearing comfort and robustness against the wearer's body temperature change.

With external mounting, the sensing elements are commonly attached to the bottom of the footwear. Such external mounting allows the sensors to have direct contact with the walking surface and is commonly used in measuring shoe-ground interactions. However, the sensing elements are exposed to the environment and the height of the footwear is increased, which may affect the natural gait of the wearer.

SUMMARY

In one embodiment, the present invention involves providing a sensor configured to measure shear ground reaction forces ("GRFs"). In one embodiment, the sensor is configured to measure biaxial GRFs. In one embodiment, the sensor includes a board (e.g., a printed circuit board) and first and second sensor units arranged on the board. In one embodiment, the first sensor unit has a first light source (e.g., a light emitting diode) and a first light receiver (e.g., a photodiode) for receiving light emitted from the first light source, while the second sensor unit has a second light source (e.g., a light emitting diode) and a second light receiver (e.g., a photodiode) for receiving light emitted from the second light source. In one embodiment, the sensor also includes a curtain plate movably mounted over the board such that it is movable in directions substantially parallel relative to the board. The curtain plate has first and second curtains projecting therefrom. The first curtain is positioned between the first light source and the first light receiver for adjusting the amount of light received by the first light receiver from the first light source based on movement of the first curtain, while the second curtain is positioned between the second light source and the second light receiver for adjusting the amount of light received by the second light receiver from the second light source based on movement of the second curtain. The first and second curtains are movable conjointly with each other in a first direction (e.g., an X direction) in response to application of a ground reaction force sensed by the curtain plate such that the amount of light received by the first light receiver from the first light source is inversely proportional to the amount of light received by the second light receiver from the second light source. The first and second light receivers are connected to a microprocessor via a wired mechanism or a wirelessly mechanism for processing signals generated by the first and second light receivers based on the amount of light received from the first and second light sources, respectively, and determining the amount of the ground reaction force.

In one embodiment, the first and second sensor units are arranged along in a second direction (e.g. a Y direction) substantially orthogonal to the first direction. When the first curtain is in its neutral position relative to the first light source and the first light receiver, the second curtain is also in its neutral position relative to the second light source and the second light receiver. When the first curtain moves in the first direction to increase the amount of light received by the first light receiver from the first light source, the second curtain moves in the first direction to proportionally decrease the amount of light received by the second light receiver from the second light source, and vice versa.

In another embodiment, the sensor includes third and fourth sensor units arranged on the board. In one embodiment, the third sensor has a third light source (e.g., a light emitting diode) and a third light receiver (e.g., a photodiode) for receiving light emitted from the third light source, while the fourth sensor unit has a fourth light source (e.g., a light emitting diode) and a fourth light receiver (e.g., a photodiode) for receiving light emitted from the fourth light source. In one embodiment, the curtain plate has third and fourth curtains. The third curtain is positioned between the third light source and the third light receiver for adjusting the amount of light received by the third light receiver from the third light source based on movement of the third curtain, while the fourth curtain is positioned between the fourth light source and the fourth light receiver for adjusting the amount of light received by the fourth light receiver from the fourth light source based on movement of the fourth curtain. The third and fourth curtains are movable conjointly with each other in the second direction (e.g., the Y direction) in response to application of a ground reaction force sensed by the curtain plate such that the amount of light received by the third light receiver from the third light source is inversely proportional to the amount of light received by the fourth light receiver from the fourth light source. The third and fourth light receivers are connected to a microprocessor via a wired mechanism or a wirelessly mechanism for processing signals generated by the third and fourth light receivers based on the amount of light received from the third and fourth light sources, respectively, and determining the amount of the ground reaction force.

In one embodiment, the third and fourth sensor units are arranged along the first direction (e.g. the X direction), which is substantially orthogonal to the second direction such that when the third curtain is in its neutral position relative to the third light source and the third light receiver, the fourth curtain is also in its neutral position relative to the fourth light source and the fourth light receiver. When the third curtain moves to increase the amount of light received by the third light receiver from the third light source, the fourth curtain moves to proportionally decrease the amount of light received by the fourth light receiver from the fourth light source, and vice versa.

In one embodiment, one or more optoelectronic sensors are embedded or otherwise incorporated into an outsole of footwear (such as boots, shoes, sneakers, etc.). Because the weight of the sensor is minimal and the original dimensions of the footwear are not altered, the sensors are less likely to affect the wearer's natural gait than externally-mounted designs. In addition, because the sensors are embedded in the outsole, they are well-suited for capturing shear GRFs. In one embodiment, a calibration method is provided for calibrating the optoelectronic sensors.

In one embodiment, the outsole-embedded optoelectronic sensors are configured to accurately measure GRFs acting on the lower extremity in operationally relevant environments. For instance, the outsole-embedded optoelectronic sensors can be used to gain an understanding of the biomechanical mechanisms underlying overuse ankle/foot injuries in military personnel. In turn, the collected data can be used to train machine learning predictive models to capture quantitative markers of incipient overuse injuries before they occur, thereby allowing appropriate team leaders to take appropriate actions (e.g., temporarily reducing the training intensity in a soldier or trainee) to reduce the incidence of such injuries.

In one embodiment, embedded electronics attached to the footwear are configured to map voltage signals from the sensors into estimates of GRFs through pre-calibrated computational models. In one embodiment, data can be stored in a local storage device, such as a microSD card, and/or be streamed wirelessly (e.g., via Wi-Fi) to a graphical user interface on a computer (e.g., phone/tablet app). These data-series inform predictive models of overuse ankle/foot injuries, which allow team leaders to monitor each team member's performance and risk for overuse injuries and timely modulate the training intensity to reduce the risk of injuries.

Besides the application in the military sector, the wearable sensing technology disclosed herein can be applied to other personnel who regularly performs loaded walking tasks and is therefore at risk for ankle/foot overuse injuries, including firefighters, construction workers, and recreational hikers. In addition, the sensors disclosed herein can provide real-time feedback signals for closed-loop control of robotic prostheses and exoskeletons, thereby potentially benefiting lower-extremity amputees and people with impaired ambulatory by informing more natural control strategies for these devices.

In summary, the present invention involves an outsole embedded optoelectronic sensor for footwear, either as an original component part or as a retrofitted part. Whether original with the footwear or retrofitted, the sensor is adapted to measure biaxial shear ground reaction forces during locomotion. Such measurements are useful for closed loop control of lower extremity robotic exoskeletons, as well as for estimation of net joint torques and approximate muscle forces. In use, in unconstrained real life environments, the optoelectronic sensor of the present invention can function to identify (and potentially prevent) mechanisms of lower extremity injuries in, for instance, soldiers and other individuals with chronic ankle instability. For such uses of the present invention, the optoelectronic sensing unit or units can be retrofitted in an outsole of existing footwear (e.g., boots, shoes, sneakers, etc.). In view of the foregoing summary, another aspect of the present invention involves a method for retrofitting existing footwear with one or more optoelectronic sensing units constructed in accordance with the present invention.

BRIEF DESCRIPTION OF THE DRAWINGS

For a better understanding of the present invention, reference is made to the following detailed description of various exemplary embodiments considered in conjunction with the accompanying drawings, in which:

FIG. 3D shows a static testbed setup in accordance with one embodiment;

DETAILED DESCRIPTION OF EXEMPLARY EMBODIMENTS

Figure 1A:
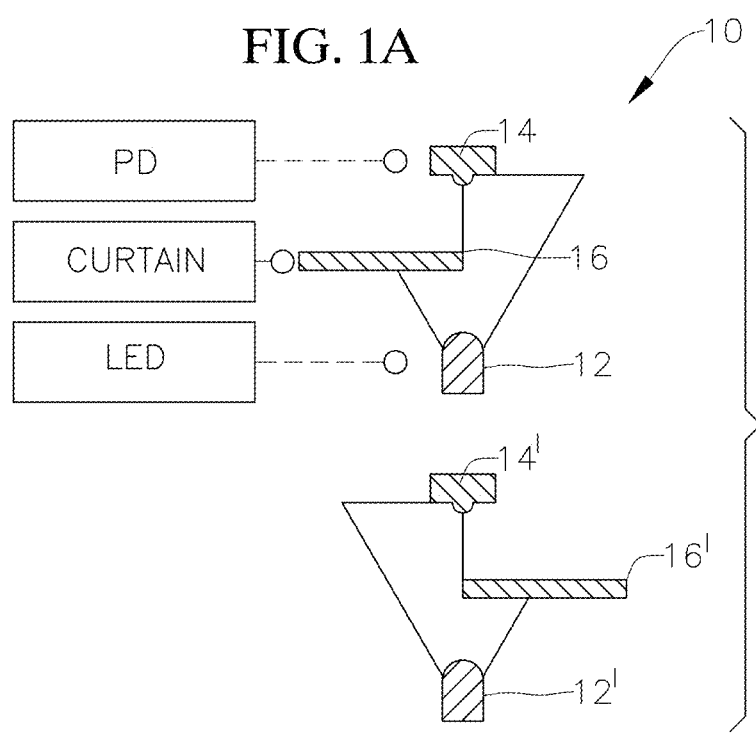
FIG. 1A is a schematic illustration of an optoelectronic sensor having opposite light emitting diode ("LED") and photodiode ("PD") pairs with curtains in neutral position in accordance with one embodiment.

Embodiments are now discussed in more detail referring to the drawings that accompany the present application. In the accompanying drawings, like and/or corresponding elements are referred to by like reference numbers.

Various embodiments are disclosed herein; however, it is to be understood that the disclosed embodiments are merely illustrative of the disclosure that can be embodied in various forms. In addition, each of the examples given in connection with the various embodiments is intended to be illustrative, and not restrictive. Further, the figures are not necessarily to scale, and some features may be exaggerated to show details of particular components (and any size, material and similar details shown in the figures are intended to be illustrative and not restrictive). Therefore, specific structural and functional details disclosed herein are not to be interpreted as limiting, but merely as a representative basis for teaching one skilled in the art to variously employ the disclosed embodiments.

Subject matter will now be described more fully hereinafter with reference to the accompanying drawings, which form a part hereof, and which show, by way of illustration, specific example embodiments. Subject matter may, however, be embodied in a variety of different forms and, therefore, covered or claimed subject matter is intended to be construed as not being limited to any example embodiments set forth herein; exemplary embodiments are provided merely to be illustrative. Among other things, for example, subject matter may be embodied as methods, devices, components, or systems. The following detailed description is, therefore, not intended to be taken in a limiting sense.

Throughout the specification and/or claims, terms may have nuanced meanings suggested or implied in context beyond an explicitly stated meaning. Likewise, the phrase "in one embodiment" as used herein does not necessarily refer to the same embodiment and the phrases "in another embodiment" and "other embodiments" as used herein do not necessarily refer to a different embodiment. It is intended, for example, that covered or claimed subject matter include combinations of example embodiments in whole or in part.

In general, terminology may be understood at least in part from usage in context. For example, terms, such as "and", "or", or "and/or," as used herein may include a variety of meanings that may depend at least in part upon the context in which such terms are used. Typically, "or" if used to associate a list, such as A, B, or C, is intended to mean A, B, and C, here used in the inclusive sense, as well as A, B, or C, here used in the exclusive sense. In addition, the term "one or more" as used herein, depending at least in part upon context, may be used to describe any feature, structure, or characteristic in a singular sense or may be used to describe combinations of features, structures or characteristics in a plural sense. Similarly, terms, such as "a," "an," or "the," again, may be understood to convey a singular usage or to convey a plural usage, depending at least in part upon context. In addition, the term "based on" may be understood as not necessarily intended to convey an exclusive set of factors and may, instead, allow for existence of additional factors not necessarily expressly described, again, depending at least in part on context.

I. SENSOR CONSTRUCTION AND OPERATION

In one embodiment, an optoelectronic sensor 10 (see FIGS. 1A-1E) is provided in an outsole of footwear (e.g., shoes, boots, sneakers, etc.) for measuring biaxial shear ground reaction force ("GRF"). In one embodiment, the operation of the sensor 10 is based on the change in the intensity of the optical coupling between a light emitting diode ("LED") 12 and a photodiode ("PD") 14 when an opaque curtain 16 moves perpendicularly to the light path (see FIGS. 1A and 1B). In accordance with one embodiment, FIG. 1A shows the top view of two opposite LED-PD pairs 12, 14 and 12', 14' with opaque curtains 16, 16' in neutral positions. The curtains 16, 16' are attached orthogonally to a surface or plate 18 (see FIGS. 1C and 1D) that is parallel to a circuit board 20 (or another suitable supporting board) containing or supporting the LEDs and PDs. The plate 18 is supported on one or more support posts 22 (see FIG. 1D) attached to the circuit board 20 such that it is able to move independently of the circuit board 20. When a shear force (uniaxial or biaxial) is applied on the plate 18, the curtains 16, 16' move conjointly and therefore simultaneously with the plate 18 in the same direction (see FIG. 1B). In one embodiment, when one of the curtains 16 moves away from its neutral position to allow more light to transmit between a corresponding one the LED-PD pairs, the other curtain 16' moves by the same distance to restrict light transmission between the other LED-PD pair. This results in a negative correlation between the intensities of the optical couplings of the two LED-PD pairs 12, 14 and 12', 14', which enables rejection of common-mode noise. Common-mode noise rejection can be achieved using regression models during a sensor calibration process.

Figure 1B:
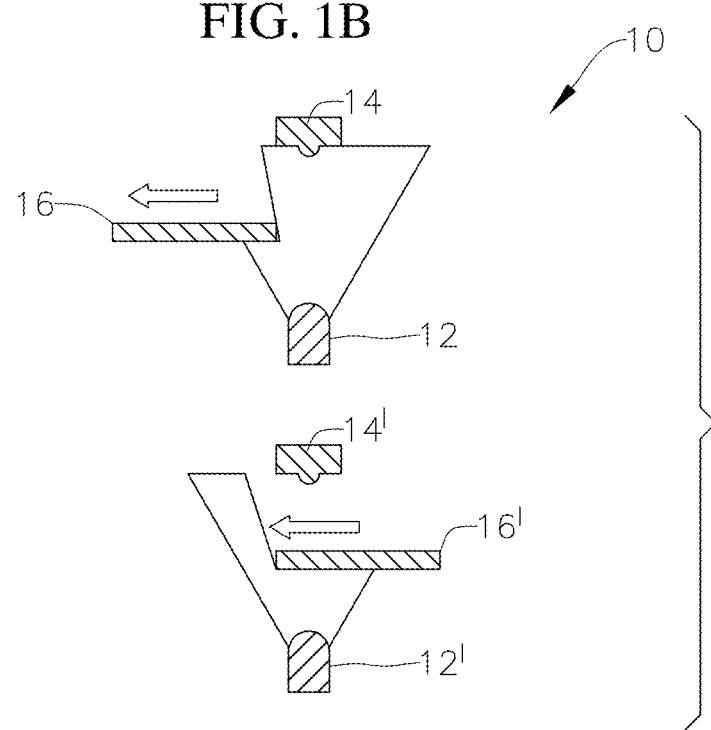
FIG. 1B is a schematic illustration of the optoelectronic sensor shown in FIG. 1A, showing effects of applying a shear force between the curtains and the LED-PD pairs.
Figure 1C:
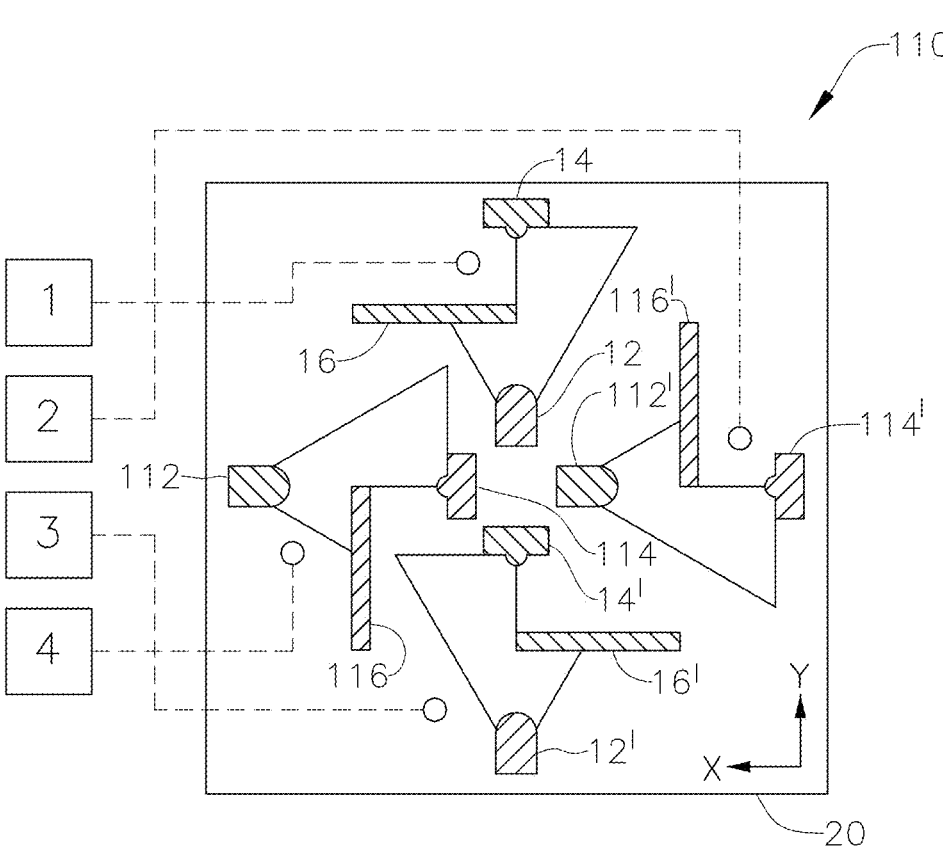
FIG. 1C is a schematic illustration of an optoelectronic sensor having a set of opposing LED-PD pairs for measuring GRFs in an X direction and a set of opposing LED-PD pairs for measuring GRFs in a Y direction in accordance with one embodiment.
Figure 1D:
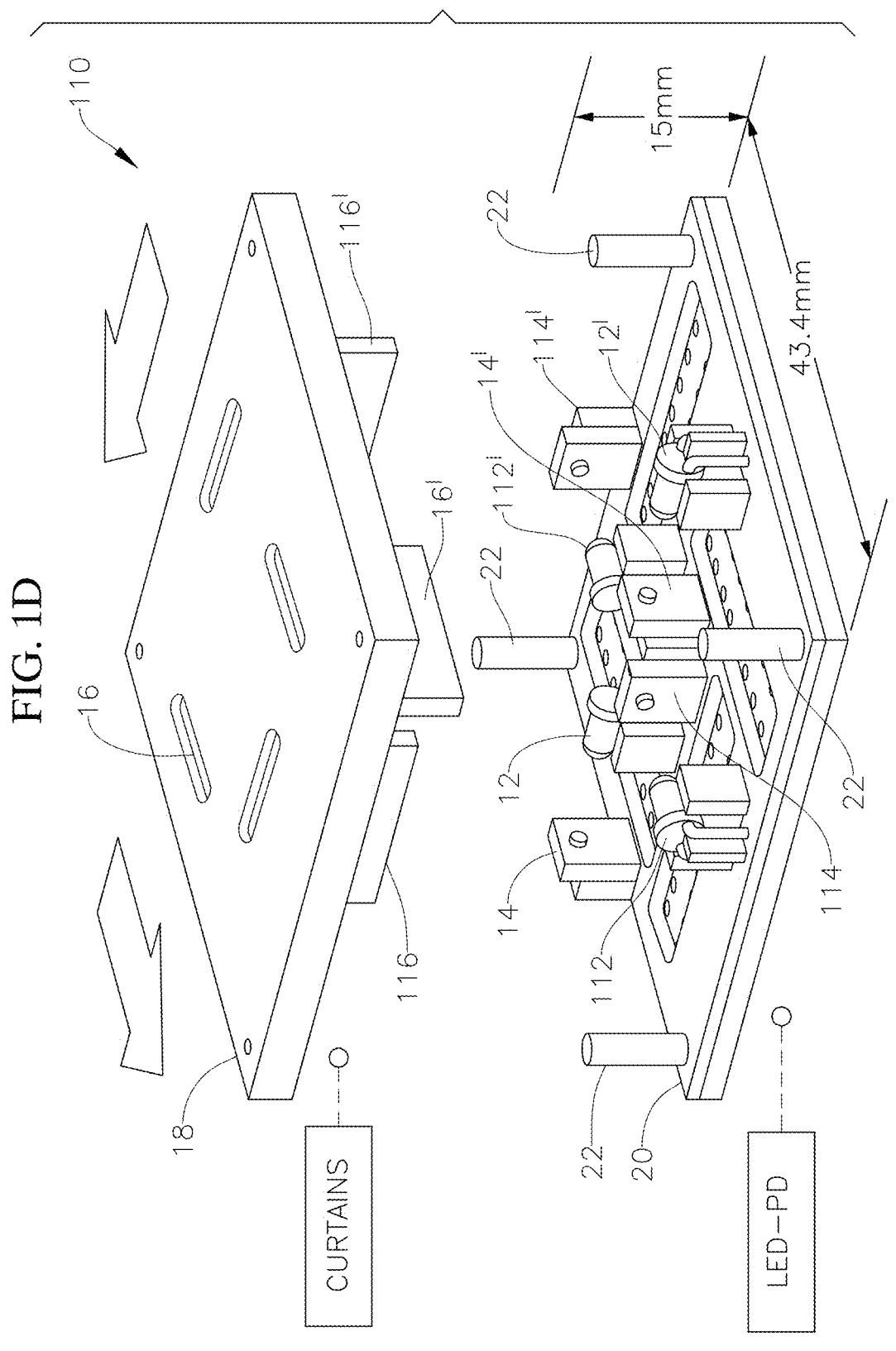
FIG. 1D is a schematic, perspective view of an optoelectronic sensor assembly having a printed circuit board with LED-PD pairs and a curtain plate in accordance with one embodiment.
Figure 1E:
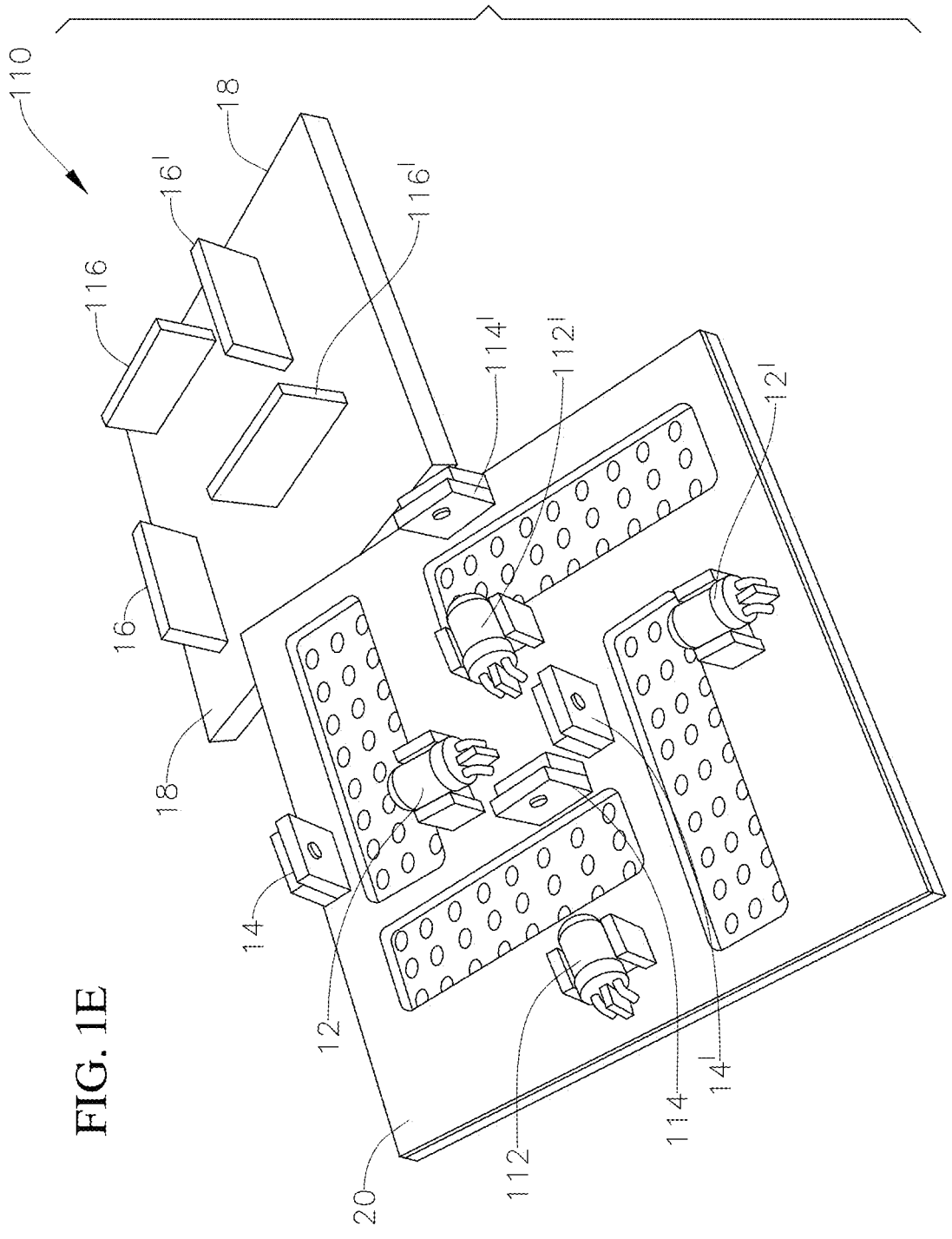
FIG. 1E is a perspective view of the sensor assembly shown in FIG. 1D.

In one embodiment, the LED-PD configuration is expanded to sense biaxial shear forces by duplicating the assembly shown in FIG. 1A and rotating it clockwise by 90 degrees, as shown in FIGS. 1C-1E. In this embodiment, an optoelectronic sensor 110 includes a set of opposing LED-PD pairs (12, 14 and 12', 14') for measuring GRFs in an X direction and another set of opposing LED-PD pairs (112, 114 and 112', 114') for measuring GRFs in a Y direction. Signals generated by each of the LED-PD pairs are used to determine the amount of GRFs applied to the footwear in which the sensor 110 is placed, it being noted that corresponding parts having the same basic structure and functionality are represented in FIGS. 1C-1E by reference numbers corresponding to their counterparts in FIGS. 1A and 1B but increased by one hundred.

Figure 2:
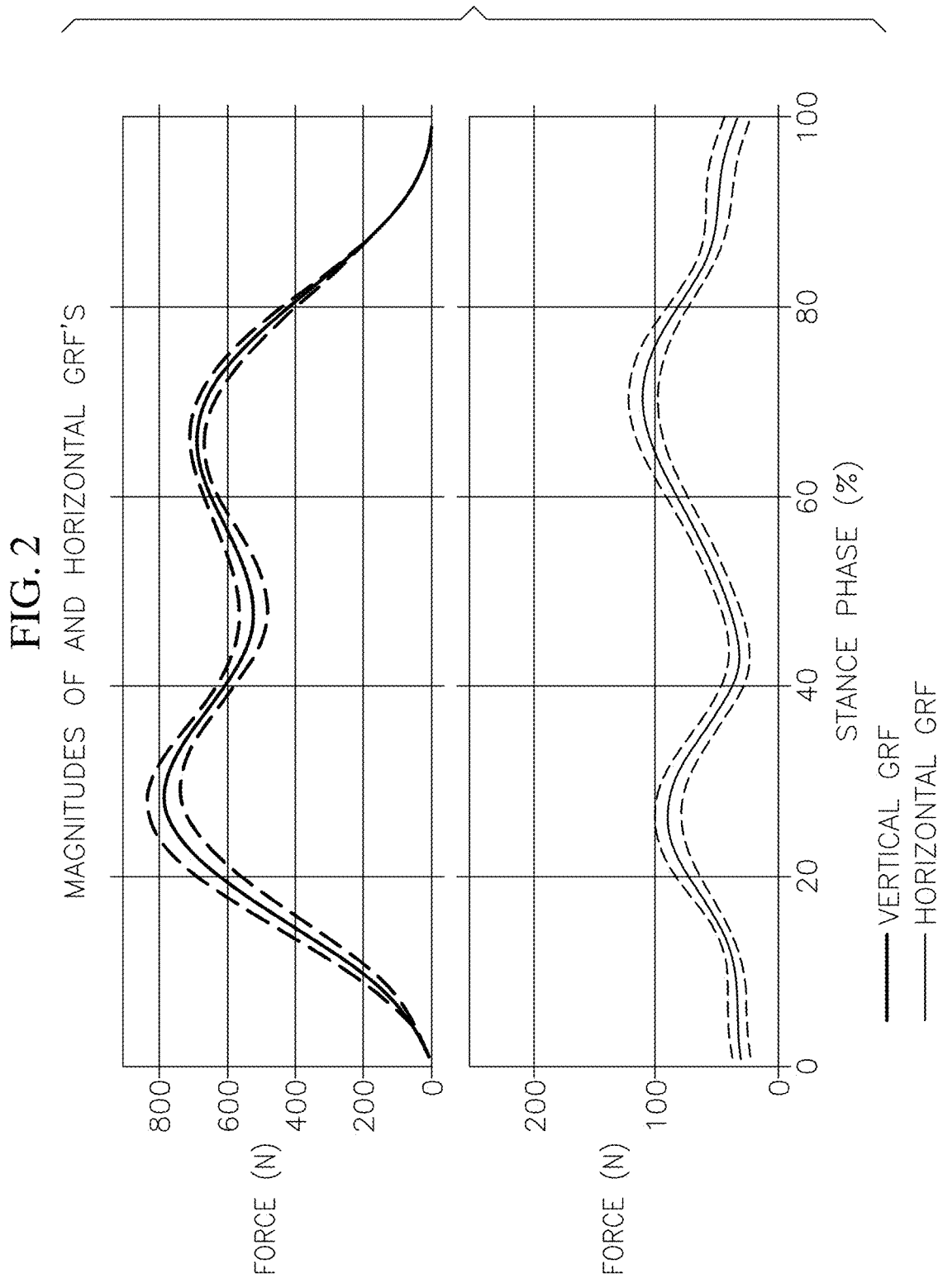
FIG. 2 illustrates average magnitudes of vertical and horizontal GRFs during a two-minute walking task at comfortable speed, dashed lines indicating +/− 1SD.

Preliminary tests and finite element analysis ("FEA") were conducted to identify the design requirements in terms of peak GRFs and corresponding strain levels to be expected in a boot outsole during locomotion. To this end, one healthy male subject (74 kg, 168 cm) was recruited to walk on a dual-belt treadmill instrumented with force plates (Bertec ITC-11-20L) at preferred speed for two minutes. The maximum GRFs measured during the test were used as the inputs to a FEA model to estimate the maximum deformation of the boot outsole during a walking task. To simulate the loading conditions of the outsole in the stance phase, the bottom surface of the FEA model was fixed in all three directions and the maximum applied normal and shear forces on the top surface of the outsole were 865 N and 250 N, respectively, as determined from experimental data (see FIG. 2). These forces were the resultants of uniform stress applied on the top surface of the outsole. Further, the geometry of the outsole model was designed to replicate a real boot outsole. Shore 80A styrene-butadiene rubber (SBR), which has the typical hardness of most commercial outsoles, was chosen as the material of the model. The results of the FEA showed that the maximum deformed displacements of the top surface relative to the bottom surface of the outsole model were 0.9 mm and 1.2 mm in vertical and horizontal directions, respectively.

In the embodiment of FIGS. 1A and 1B, the optoelectronic sensor 10 comprises at least two components: the circuit board 20 and the curtain plate 18. In the embodiment of FIGS. 1C-1E, the circuit board 20 contains four LED-PD pairs (12, 14; 12', 14'; 112, 114 and 112', 114'), wherein accurate alignment can be achieved by adding the curtain plate 18 (e.g., a custom 3D printed offset curtain plate). In this embodiment, the curtain plate 18 therefore includes a base and four curtains 16, 16', 116, 116'. In other embodiments, the curtain plate 18 can be fabricated from opaque cast acrylic material using laser cutting or from any other suitable materials using any conventional process. The posts 22, which includes rubber contacts, support the curtain plate 18 in the vertical direction and constrain relative rotations between the two parallel plates (i.e., the circuit board 20 and the curtain plate 18). The curtain plate 18 is configured to move in directions substantially parallel to the circuit board 20 (i.e., in X and Y directions). In one embodiment, a different number of LED-PD pairs and/or curtains can be used.

Figure 3A:
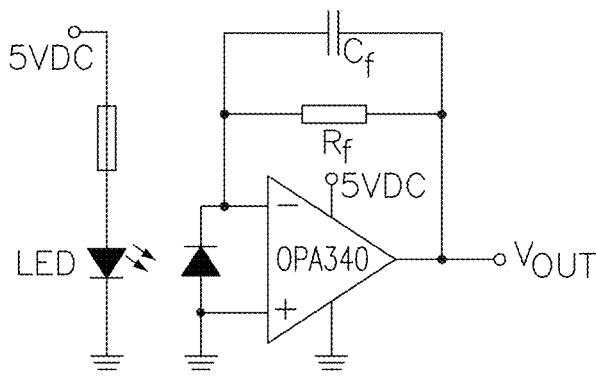
FIG. 3A is a schematic diagram of a transimpedance amplifier circuit of an optoelectronic sensor in accordance with one embodiment.
Figure 3B:
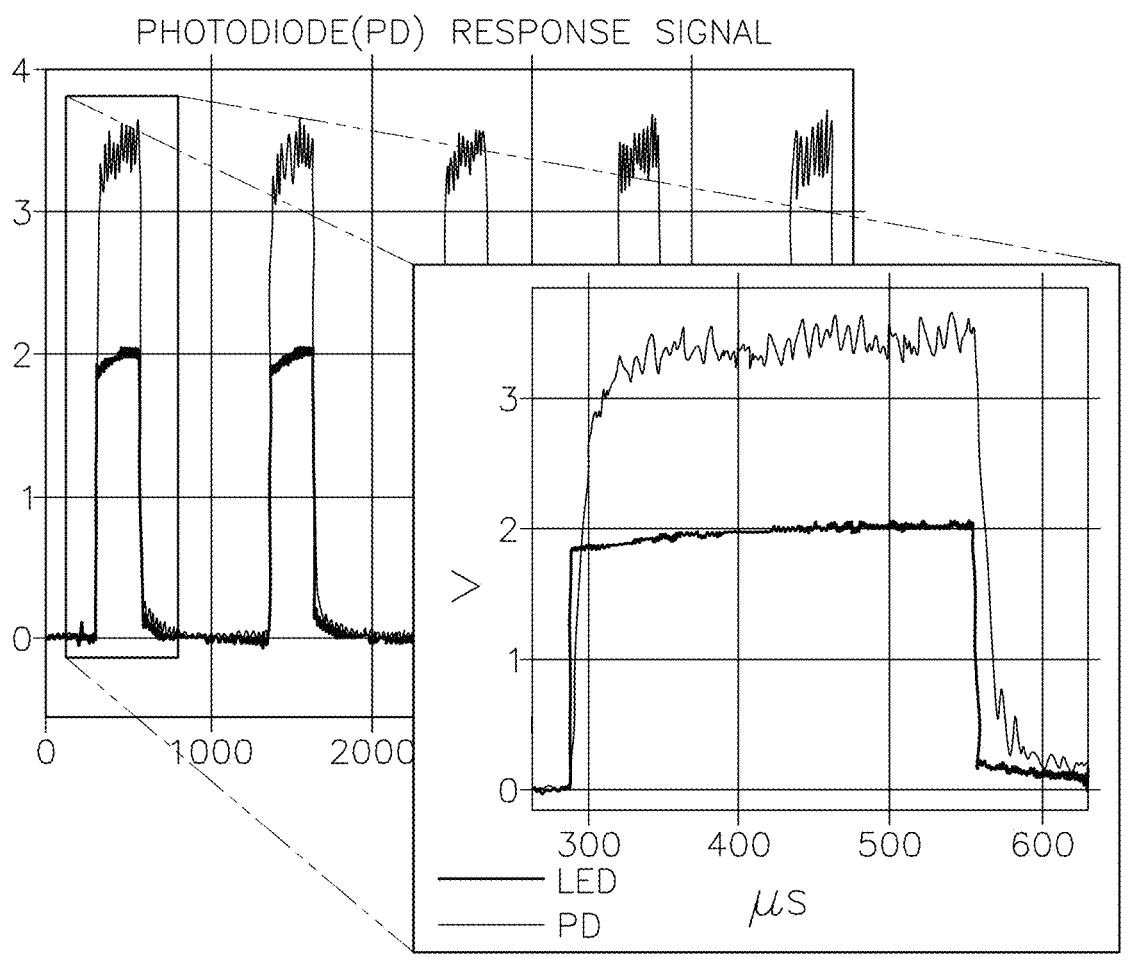
FIG. 3B illustrates a PD response to a square-wave LED activation signal (f=1 kHz, duty cycle 0.25) of a LED-PD pair of an optoelectronic sensor in accordance with one embodiment.

In one embodiment, in order to acquire sensor data at 1 kHz and prevent each LED-PD pair from being affected by the light emitted from other LEDs, LEDs are turned on/off sequentially, using 4 square-wave activation signals (f=1 kHz, duty cycle=0.25, 250 μs time offset). In one embodiment, to achieve stable, fast, and low-noise response, the current generated by each PD is converted and amplified to a measurable voltage output through a transimpedance amplifier circuit, as shown in FIG. 3A. In one embodiment, the main components of the circuit include a single-supply, rail-to-rail operational amplifier (such as the one available as "OPA340", from Texas Instruments Inc., Texas, USA), and a silicon PIN photodiode (such as the one available as "OP950" from TT Electronics Plc., Woking, UK). In one embodiment, a 650 nm red LED (such as the one available from Marktech Optoelectronics, New York, USA) is used as the emitter source. In one embodiment, feedback resistor $R_f$ and capacitor $C_f$ are tuned to achieve a desirable output response. FIG. 3B shows a sample response signal of an LED-PD pair. The time constant of the response signal is approximately 13 μs.

Figure 4:
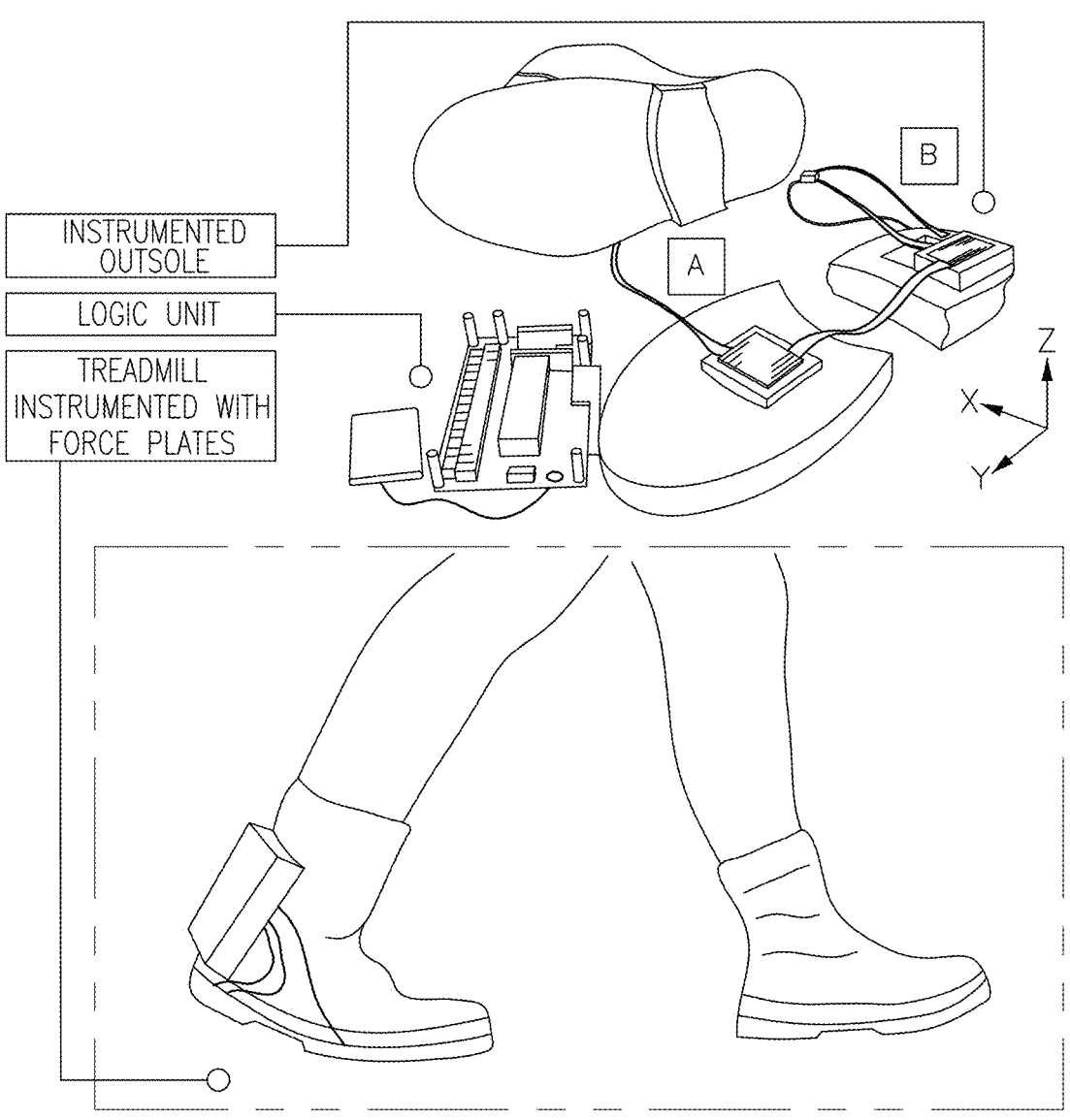
FIG. 4 illustrates an outsole implementation and walking experiment in accordance with one embodiment, reference letters A and B indicating anterior and posterior optoelectronic sensors.
Figure 4A:
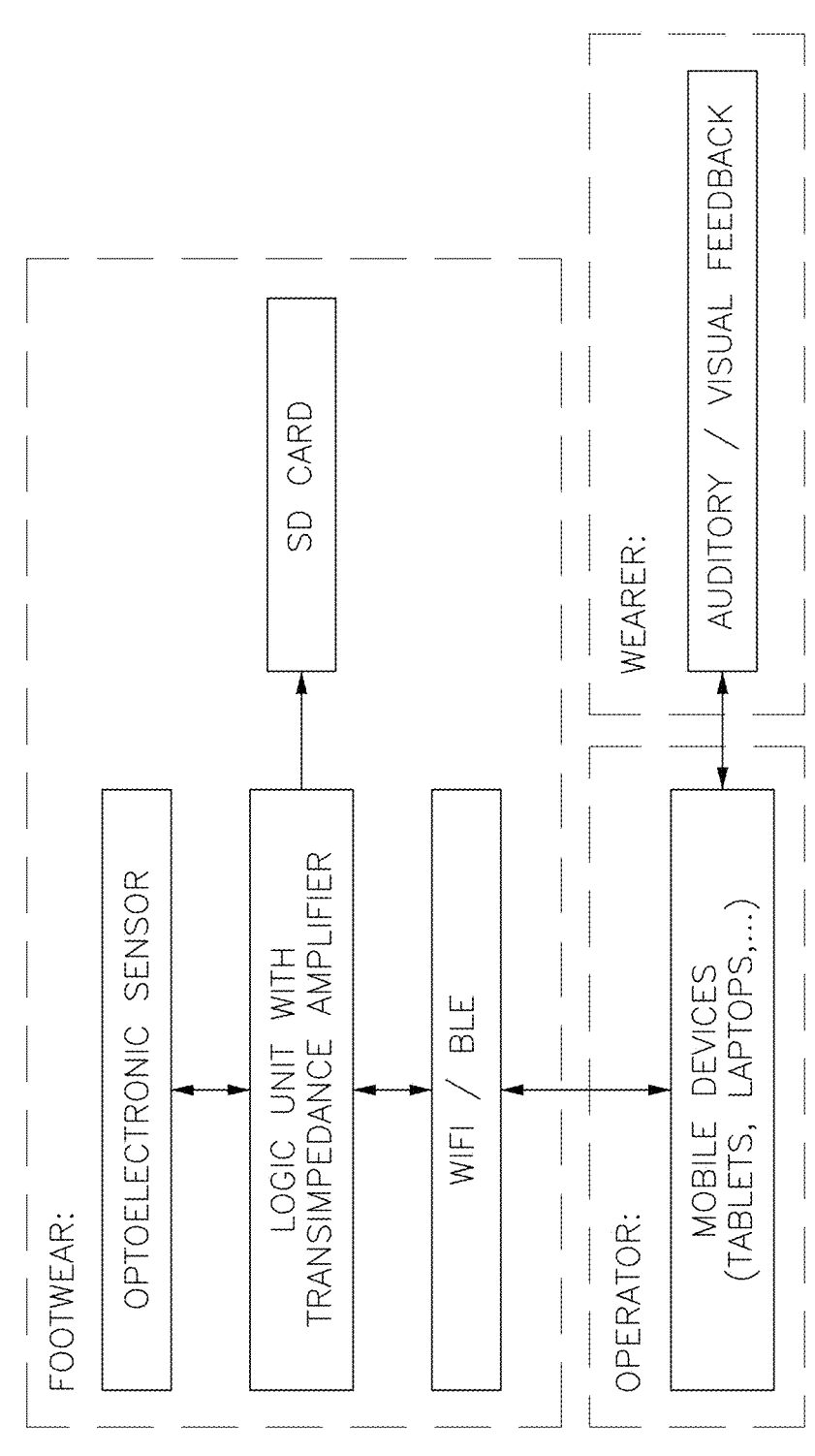
FIG. 4A is a schematic diagram illustrating various components used in conjunction with an optoelectronic sensor in accordance with one embodiment.

In one embodiment, two sensors were assembled and embedded into the outsole of a right boot, as shown in FIG. 4A. In another embodiment, only one sensor or more than two sensors can be embedded in the boot's outsole. In one embodiment, the original boot outsole was removed and replaced with a custom outsole (e.g., Shore 80A SBR), which was cut to replicate its dimensions. In one embodiment, sensor readings are acquired by a custom-engineered logic unit, which consists of a 32-bit microcontroller (e.g., ARM Cortex-M4F, PJRC, Oregon, USA) and eight transimpedance amplifier circuits. In one embodiment, the circuit is powered by a battery (e.g., a 3.7V, 1000 mAh Li—Po battery) through a 5V step-up voltage regulator. In one embodiment, data are sampled at 1 kHz with a 13-bit ADC embedded in the microcontroller, low-pass filtered, and streamed to a portable data-logger at 500 Hz via an onboard Wi-Fi module (XBee Wi-Fi S6B, Digi Inc., Minnesota, USA). In one embodiment, the data-logger is an off-the-shelf single-board Linux computer (ODROID-C2, Hardkernel Co., GyeongGi, South Korea). In one embodiment, data are also streamed to a graphical user interface on the experimenter's laptop. In one embodiment, the overall weight of the two shear force sensors and the logic unit is approximately 150 g, which is less than 17% of the boot weight. In one embodiment, the device is wireless and fully portable.

II. PHASE-LOCKED GRF MODELS

In one embodiment, in order to extract shear GRFs from raw PD signals, phase-locked multivariate linear models can be utilized (see, e.g., the models discussed in T. T. H. Duong et al., "Improving the Accuracy of Wearable Sensors for Human Locomotion Tracking Using Phase-Locked Regression Models," IEEE International Conference on Rehabilitation Robotics, 2019, the entire disclosure of which is incorporated herein by reference and made part hereof). These models are computationally inexpensive and therefore suitable for on-line implementation in embedded systems. Further, the models leverage existing methods for on-line estimation of the gait phase, which have been widely used in the control of lower-extremity exoskeletons and powered orthoses (see, e.g., L. Righetti et al., "Adaptive Frequency Oscillators and Applications," The Open Cybernetics and Systemics Journal, 3, pp: 64-69, 2009, and T. Petric et al., "On-line frequency adaptation and movement imitation for rhythmic robotic tasks," The International Journal of Robotics Research, 30 (14), pp: 1775-1788, 2011, the entire disclosures of which are incorporated herein by reference and made part hereof).

In one embodiment, the stance phase is discretized into a set of N=101 equally-spaced data points (0-100%). Then, two sets of N independent linear models are applied to extract shear forces along the anteroposterior (Y) and mediolateral (X) directions:

$$\hat{F}_i^X = \bar{\beta}_{0,i}^X = \bar{\beta}_{1,i}^X PD_i^{1A} + \bar{\beta}_{2,i}^X PD_i^{3A} + \bar{\beta}_{3,i}^X PD_i^{1B} + \bar{\beta}_{4,i}^X PD_i^{3B}, i \in [1, N] \quad (1)$$

$$\hat{F}_i^Y = \bar{\beta}_{0,i}^Y = \bar{\beta}_{1,i}^Y PD_i^{2A} + \bar{\beta}_{2,i}^Y PD_i^{4A} + \bar{\beta}_{3,i}^Y PD_i^{2B} + \bar{\beta}_{4,i}^Y PD_i^{4B}, i \in [1, N] \quad (2)$$

$$\hat{F}_i^X \text{ and } \hat{F}_i^Y$$

are the estimated shear forces along the X and Y axes of the boot's local frame (FIG. 4).

$$\bar{\beta}_{*,i}^X \text{ and } \bar{\beta}_{*,i}^Y$$

are the regression coefficients of the ith models and $PD_i$ are the signals of the corresponding PDs at the i % of the stance phase. To train and test these models, data were concurrently collected with the wearable device and with validated laboratory equipment (which served as the reference system) during treadmill walking tasks at various speeds. The experimental procedure is described below in Sec. III-B.

Figure 3C:
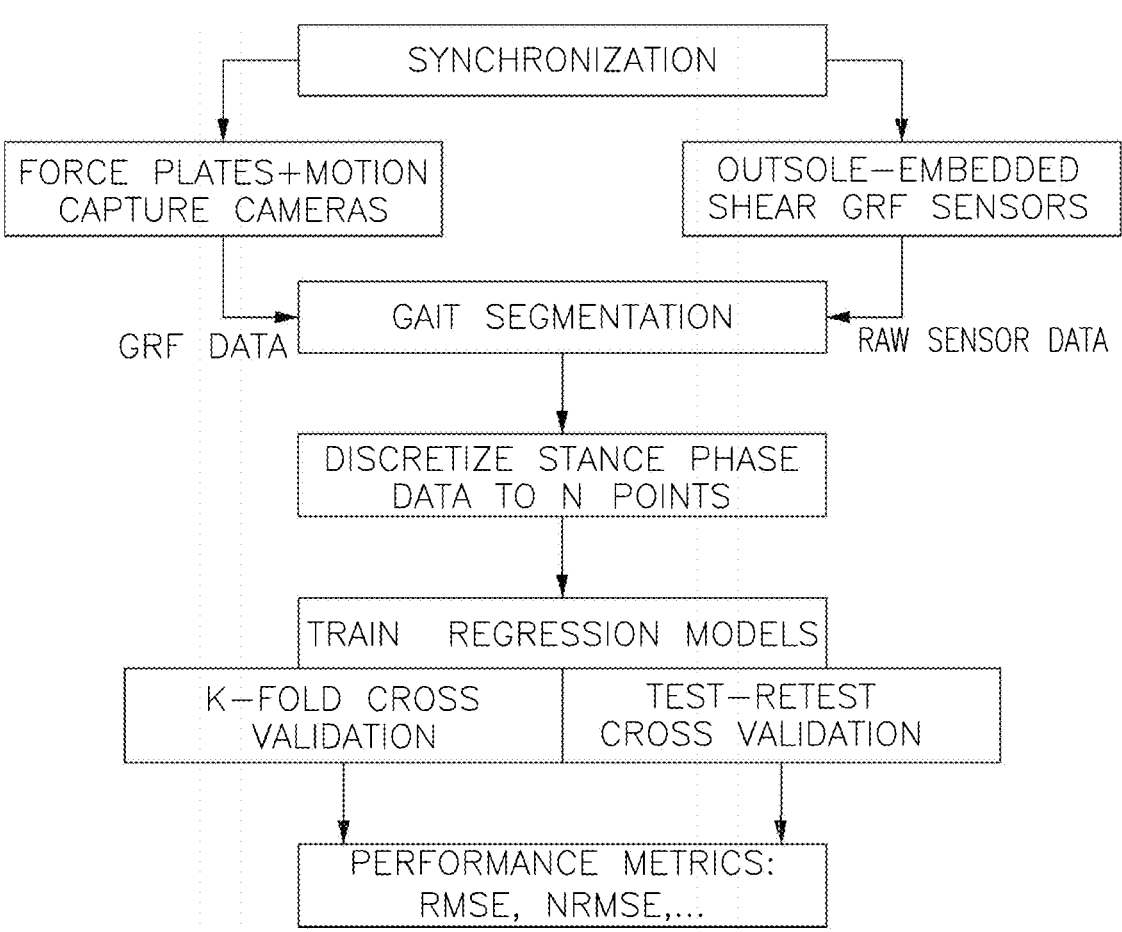
FIG. 3C is a flow diagram illustrating calibration and training processes in accordance with one embodiment.

In one embodiment, the calibration and training processes illustrated in FIG. 3C may be utilized. In one embodiment, data are initially collected from a reference system (force plates and motion capture cameras) and one or more outsole-embedded optoelectronic sensors 10, which are time-synchronized with the reference system. In another embodiment, time series data are segmented into each walking stride, while GRF data in the stance phase are discretized to N=101 points (as described above). The phase-locked regression models are then trained in the form discussed above. K-fold CV, test-retest CV, and performance metrics are described in the dynamic test sections below (see also H. Zhang et al., "Accurate ambulatory Gait Analysis in Walking and Running Using Machine Learning Models", IEEE Transactions on Neural Systems and Rehabilitation Engineering, Vol. 28, No. 1, pp: 191-202, January, 2020, the entire disclosure of which is incorporated herein by reference and made part hereof).

III. EXAMPLES

A. Static Test

To validate the operating principle of the sensor, a static testbed was fabricated. The testbed included an off-the-shelf, 3-axis linear stage with micrometric precision. The stage was mounted inside a custom-designed aluminum frame, as shown in FIG. 3D. The circuit board was fixed upside down on a plate, which was attached to the frame in such a way that its surface was parallel to the top surface of the linear stage located below. The curtain plate was mounted on the top surface of the linear stage, whose displacements along three orthogonal axes could be controlled using three micrometer screw gauges. During testing, the testbed was covered with opaque rubber sheets to prevent the ambient light from entering the test area. The LEDs on the circuit board were triggered sequentially as described above. The amplified PD signals were measured and logged by an oscilloscope.

The sensitivity to both horizontal (XY) and vertical (Z) displacements were determined. To this end, the starting Z position was selected at the height where the curtains touched the surface of the circuit board and then increased to 1 mm with increments of 500 μm. The displacements along the X and Y axes spanned the interval [−1.5, 1.5] mm with increments of 100 μm. The steady-state PD voltage readings were recorded at each displacement step.

B. Dynamic Test and Data Processing

One healthy male subject (74 kg, 168 cm, 28 yrs) participated in an experiment to validate the models described in Sec. II above. The experiment involved two sessions of treadmill walking on the same instrumented treadmill used for preliminary testing (see Sec. I above). Prior to the first session, the subject donned the instrumented boots and his comfortable walking speed (CWS) was determined using the iterative procedure described in U. Dal et al., "Determination of Preferred Walking Speed on Treadmill May Lead to High Oxygen Cost on Treadmill Walking," Gait & Posture, 31 (3), pp: 366-369, 2010, the entire disclosure of which is incorporated herein by reference and made part hereof. Then, the subject walked at 85%, 100%, and 115% of CWS for a total of 6 minutes (i.e., 2 minutes for each speed). After the first walking session, the subject doffed the boots, rested for 10 minutes, then donned the system again and completed another 6-minute walking session similar to the previous one.

GRFs were recorded by the force plates embedded in the treadmill (900 Hz) and by the instrumented boots (500 Hz). Four reflective markers were attached to the boots, as shown in FIG. 4. An optical motion capture system (VICON Vero v2.2, Oxford, U.K.) with eight cameras was used to track the markers at 300 Hz. The reference system and the boots were accurately synchronized by using a custom wireless synchronization board working at 500 Hz (see, e.g., T. T. H. Duong et al., "Improving the Accuracy of Wearable Sensors for Human Locomotion Tracking Using Phase-Locked Regression Models," IEEE International Conference on Rehabilitation Robotics, 2019 (referenced above); and H. Zhang et al., "Regression Models for Estimating Kinematic Gait Parameters with Instrumented Footwear," IEEE International Conference on Biomedical Robotics and Biomechatronics, Aug. 26-29, 2018, the entire disclosure of which is incorporated herein by reference and made part hereof).

During post processing, markers data were used to map the GRFs measured by the reference system into the boot's local frame (shown in FIG. 4). GRF data were then segmented into individual strides using readings from the force plates, and the stance phase within each stride was identified. To this end, heel-strike and toe-off events were determined using a simple conventional thresholding algorithm. Finally, within each gait cycle, data from the wearable sensors and from the force plates were downsampled into N=101 equally-spaced data points, corresponding to 0-100% of the stance phase.

To validate the models presented in Sec. II, the following cross-validation approaches were applied:

1) K-Fold Cross Validation: The strides from one session were randomly split into k=10 equal bins. For each of the 10 folds, one bin was selected to be the test data, and the models were trained using the remaining 9 bins.
2) Test-Retest Validation: The models were trained using the data collected in the first session and tested on the data collected in the retest session.

The following error metrics were computed for each validation method: root-mean-squared error (RMSE), normalized root-mean squared error (NRMSE), mean absolute error (MAE), standard deviation of the error (STD), and coefficient of determination ($R^2$). In particular, NRMSE was calculated as the mean of the within-stride NRMSE values:

$$NRMSE^j = \frac{RMSE^j}{F^j_{max} - F^j_{min}} \quad (3)$$

$$RMSE^j = \sqrt{\frac{\sum_{i=1}^{N=101}\left(\hat{F}^j_i - \hat{F}^j_i\right)^2}{N}} \quad (4)$$

$F^j_{max}$ and $F^j_{min}$ are the maximum and minimum uniaxial shear forces during the jth stride.

C. Results

Figure 5:
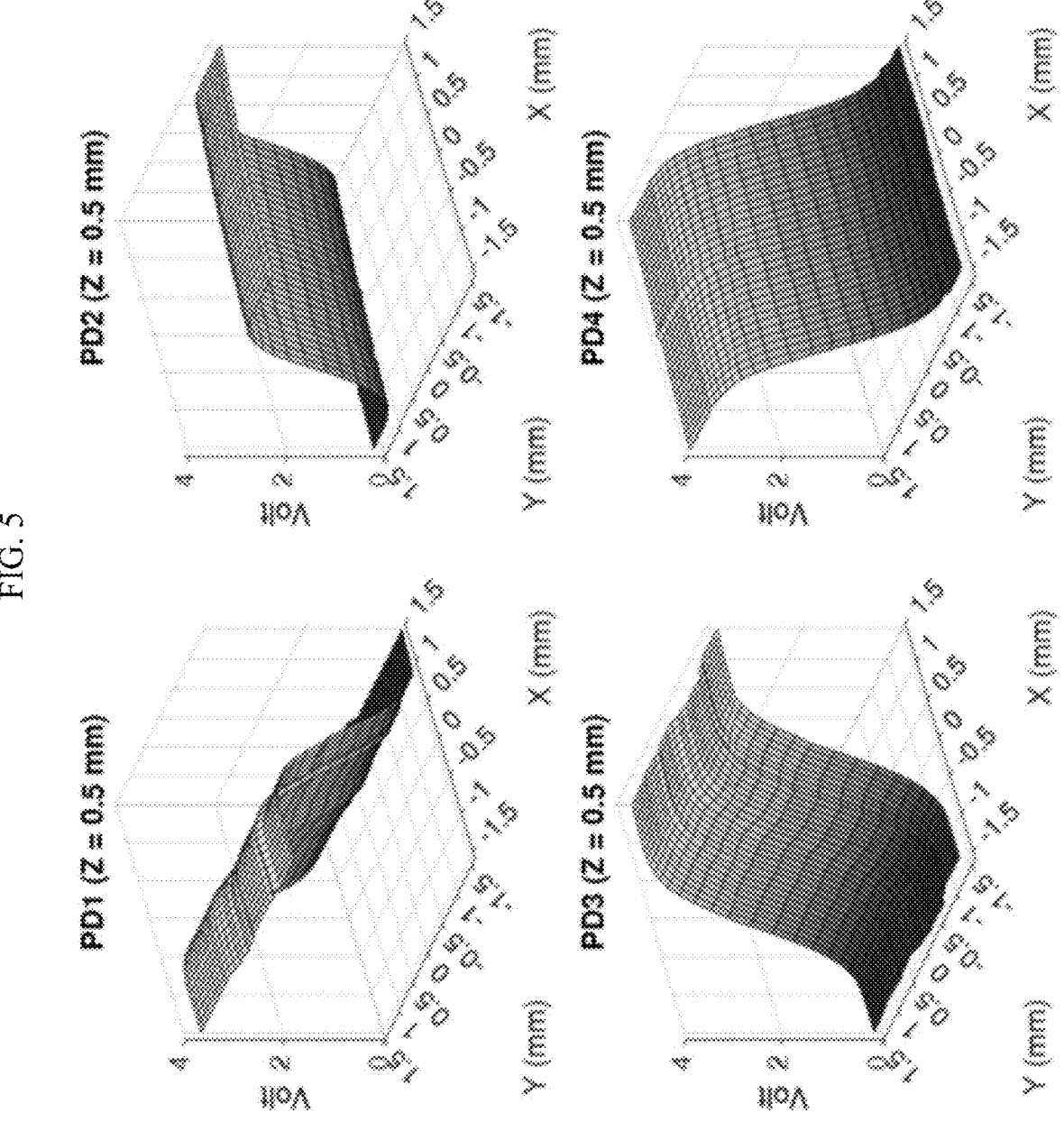
FIG. 5 illustrates responses of four PDs along the X and Y directions at Z=0.5 mm in an experiment in accordance with one embodiment.
Figure 6:
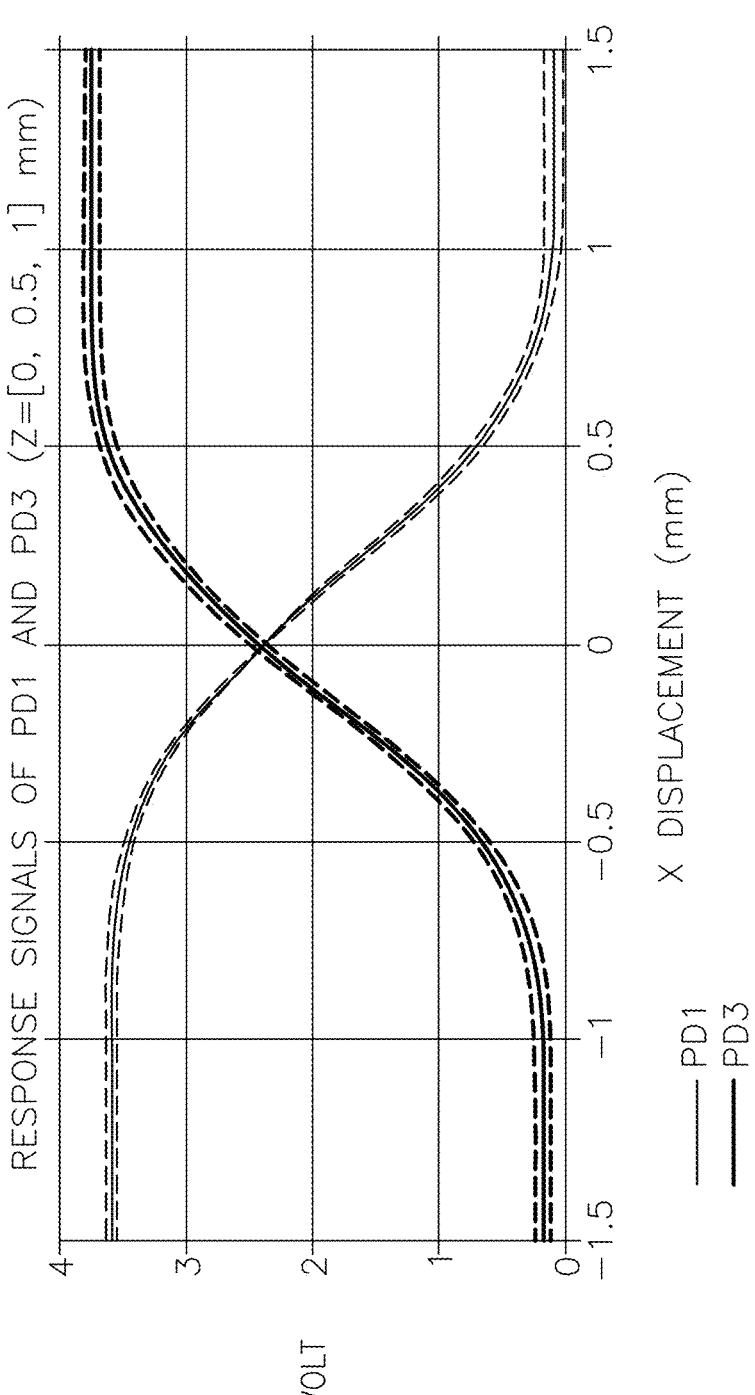
FIG. 6 illustrates responses of PD1 and PD3 vs. X displacements in an experiment in accordance with one embodiment, data from analyzed Y and Z displacements being pooled to generate these curves and dashed lines indicating +/− 1SD.

The static test resulted in a grid of 2883 data points per each PD. FIG. 5 shows the responses of the PDs as the XY displacements were adjusted from −1.5 mm to 1.5 mm, and the Z position was set at 0.5 mm from the starting position. FIG. 6 shows the mean and standard deviation of the signals measured from PD1 and PD3 across the entire static test.

12

Figure 7:
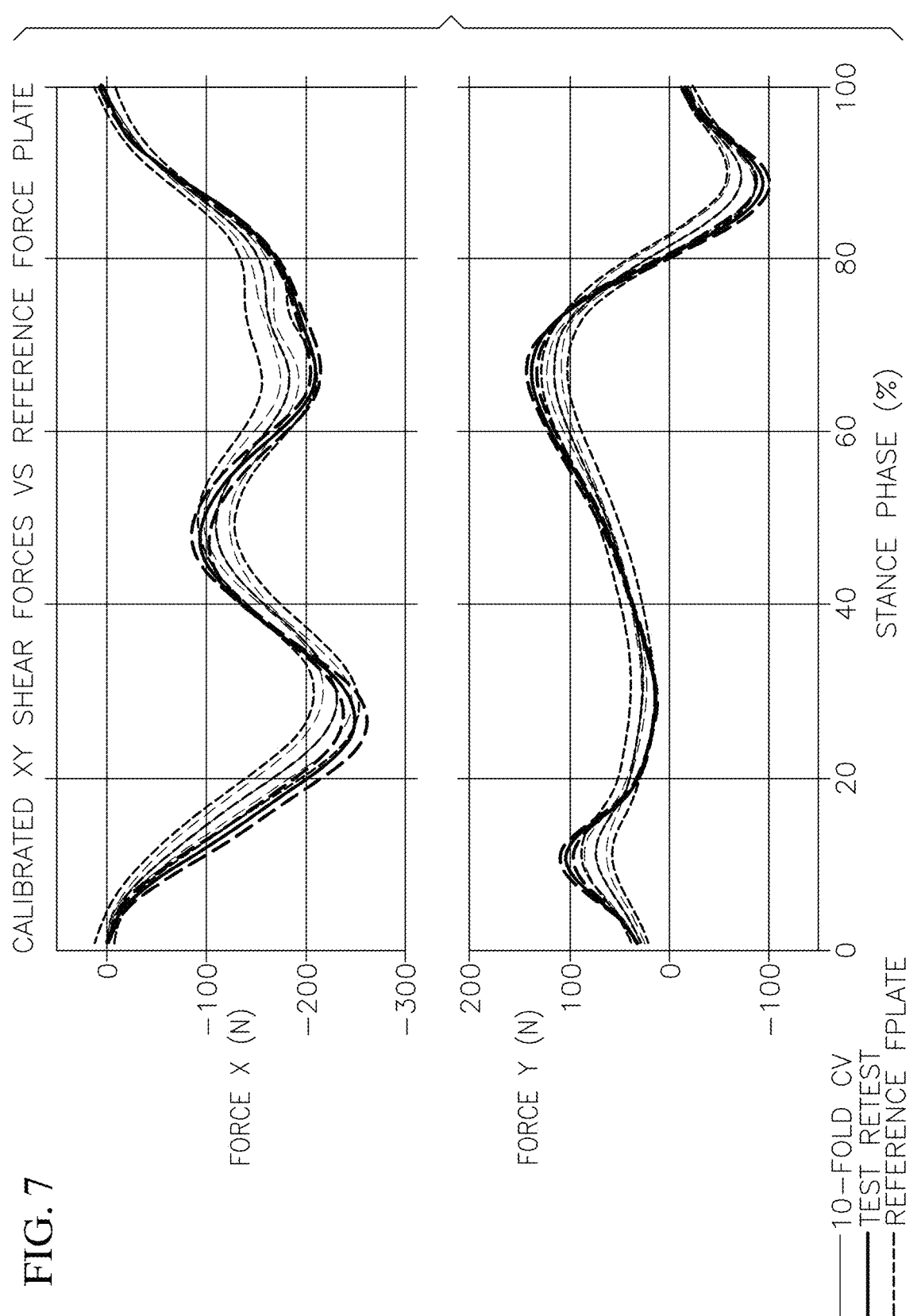
FIG. 7 illustrates shear forces measured by force plates and by instrumented boots after calibration, X and Y indicating the mediolateral and anteroposterior directions, respectively, and dashed lines indicating +/− 1SD.

In the dynamic test, subject's CWS was 1.0 m/s. A total of 730 gait cycles was concurrently collected by the instrumented boots and by the reference system. Tab. I shows the error metrics across all the test data. FIG. 7 illustrates mean and standard deviation of the shear GRFs along X and Y measured by the reference system and by the boots under the two validation models.

TABLE I

| | $F_X$ | | $F_Y$ | |
|---|---|---|---|---|
| | 10-Fold | Retest | 10-Fold | Retest |
| NRMSE | 0.07 | 0.11 | 0.05 | 0.10 |
| RMSE (N) | 17.47 | 26.97 | 10.60 | 18.92 |
| MAE (N) | 13.12 | 20.97 | 8.25 | 15.03 |
| STD (N) | 17.46 | 25.11 | 10.61 | 18.78 |
| $R^2$ | 0.97 | 0.94 | 0.98 | 0.96 |

Results from the static tests illustrated in FIG. 5 show approximately symmetrical responses in opposite pairs of PDs, as suggested by the sensor configuration shown in FIG. 1C. This behavior can be more closely observed in the responses of the mediolateral PDs shown FIG. 6. The figure also shows negligible sensitivity of the mediolateral PDs to displacements along the anteroposterior and vertical directions (as indicated by the small variability in the pooled data). Altogether, the results of the static test confirmed the operating principle of the sensor design disclosed herein.

The results obtained from the walking tests, shown in Tab. I, validate the computational models discussed above for extracting estimates of biaxial shear GRFs from raw sensor data. To test the robustness of the models, the test subject was asked to span a broad range of walking speeds (i.e., a ±0.15×CWS variation in walking speed) and don-doff the boots in-between the walking sessions. When observations from a single walking session were used to train and test the models (10-fold model), the average NRMSE was 7% and 5% for mediolateral and anteroposterior forces, respectively. These error metrics increased to 11% and 10% when previously trained models were applied to a new walking task (test-retest model). Part of these errors might be due to the nonlinear, pseudo-elastic stress/strain response of the rubber used for the boot sole, which cannot be precisely captured by the linear models used in this work. The error increase between 10-fold and test-retest models might be due to the subject changing his walking patters after the first walking session. Nonetheless, the high coefficients of determination in both models (>0.94) indicates a correlation between ground-truth GRFs and the estimates produced by the wearable system, as can also be inferred from FIG. 7.

In one embodiment, the sensor disclosed herein is lightweight and does not significantly alter the traditional structure of the footwear. As a result, it is less likely to affect the natural gait of the wearer compared to sensors attached externally (i.e., to the bottom of the outsole).

It will be understood that the embodiments described in the foregoing specification are merely exemplary and that a person skilled in the art may make many variations and modifications without departing from the spirit and scope of the present invention. For instance, other features, attributes and exemplary embodiments of the present invention are disclosed and illustrated in a paper authored by Duong et al. entitled "An Outsole-Embedded Optoeletronic Sensor to Measure Shear Ground Reaction Forces During Locomotion", which paper was presented at a conference commencing on May 31, 2020, and which paper is incorporated herein by reference in its entirety and made part hereof.

What is claimed is:

1. Sensor apparatus adapted to measure shear ground forces, comprising:
   a first light source;
   a first light receiver located in a fixed position relative to said first light source and configured to receive light emitted from said first light source, wherein said first light source and said first light receiver constitute a first sensor unit;
   a first curtain movably positioned between said first light source and said first light receiver, said first curtain being movable relative to said first light source and said first light receiver so as to adjust the amount of light received by said first light receiver from said first light source;
   a second light source;
   a second light receiver located in a fixed position relative to said second light source and configured to receive light emitted from said second light source, wherein said second light source and said second light receiver constitute a second sensor unit that is independent of said first sensor unit; and
   a second curtain movably positioned between said second light source and said second light receiver, said second curtain being movable relative to said second light source and said second light receiver so as to adjust the amount of light received by said second light receiver from said second light source, said second curtain being movable conjointly with said first curtain in a first direction such that the amount of light received by said first light receiver from said first light source is inversely proportional to the amount of light received by said second light receiver from said second light source;
   wherein the shear ground forces are in foot-worn wearable systems.

2. Sensor apparatus according to claim 1, wherein said first and second light sources and said first and second light receivers are fixedly positioned on a first mounting plate, and wherein said first and second curtains are fixedly positioned on a second mounting plate, said second mounting plate being arranged parallel to said first mounting plate and being movable in said first direction responsive to ground reaction forces sensed by said second mounting plate.

3. Sensor apparatus according to claim 2, wherein said first mounting plate includes a printed circuit board.

4. Sensor apparatus according to claim 3, wherein said first light source includes a first light emitting diode, and wherein said second light source includes a second light emitting diode.

5. Sensor apparatus according to claim 4, wherein said first light receiver includes a first photodiode, and wherein said second light receiver includes a second photodiode.

6. Sensor apparatus according to claim 2, further comprising a microprocessor configured to receive signals generated by said first and second light receivers responsive to the amount of light received from said first and second light sources, respectively, and to process said signals for the purpose of determining the amount of said ground reaction forces.

7. Sensor apparatus according to claim 1, wherein said first and second light sources and said first and second light receivers are arranged in a second direction substantially orthogonal to said first direction.

8. Sensor apparatus according to claim 7, wherein said first curtain is positionable in a first neutral position relative to said first light source and said first light receiver, and wherein said second curtain is positionable in a second neutral position relative to said second light source and said second light receiver, said first curtain assuming its said first neutral position when said second curtain assumes its said second neutral position.

9. Sensor apparatus according to claim 8, wherein when said first and second curtains move in said first direction from said first and second neutral positions, respectively, the amount of light received by said first light receiver from said first light source increases, while the amount of light received by said second light receiver from said second light source decreases, and vice versa.

10. Sensor apparatus according to claim 1, further comprising a third light source;
   a third light receiver located in a fixed position relative to said third light source and configured to receive light emitted from said third light source, wherein said third light source and said third light receiver constitute a third sensor unit;
   a third curtain movably positioned between said third light source and said third light receiver, said third curtain being movable relative to said third light source and said third light receiver so as to adjust the amount of light received by said third light receiver from said third light source;
   a fourth light source;
   a fourth light receiver located in a fixed position relative to said fourth light source and configured to receive light emitted from said fourth light source, wherein said fourth light source and said fourth light receiver constitute a fourth sensor unit that is independent of said third sensor unit; and
   a fourth curtain movably positioned between said fourth light source and said fourth light receiver, said fourth curtain being movable relative to said fourth light source and said fourth light receiver so as to adjust the amount of light received by said fourth light receiver from said fourth light source, said fourth curtain being movable conjointly with said third curtain in a second direction substantially orthogonal to said first direction such that the amount of light received by said third light receiver from said third light source is inversely proportional to the amount of light received by said fourth light receiver from said fourth light source.

11. Sensor apparatus according to claim 10, wherein said first, second, third and fourth light sources and said first, second, third and fourth light receivers are fixedly positioned on a first mounting plate, and wherein said first, second, third and fourth curtains are fixedly positioned on a second mounting plate, said second mounting plate being arranged parallel to said first mounting plate and being movable in said first direction responsive to ground reaction forces sensed by said second mounting plate.

12. Sensor apparatus according to claim 11, wherein said first mounting plate includes a printed circuit board.

13. Sensor apparatus according to claim 12, wherein said first, second, third and fourth light sources include first, second, third and fourth light emitting diodes, respectively.

14. Sensor apparatus according to claim 13, wherein said first, second, third and fourth light receivers include first, second, third and fourth photodiodes, respectively.

15. Sensor apparatus according to claim 10, further comprising a microprocessor configured to receive signals generated by said first, second, third and fourth light receivers responsive to the amount of light received from said first, second, third and fourth light sources, respectively, and to process said signals for the purpose of determining the amount of said ground reaction forces.

16. Sensor apparatus according to claim 10, wherein said first and second light sources and said first and second light receivers are arranged in said second direction, and wherein said third and fourth light sources and said third and fourth light receivers are arranged in said first direction.

17. Sensor apparatus according to claim 16, wherein said first curtain is positionable in a first neutral position relative to said first light source and said first light receiver, and wherein said second curtain is positionable in a second neutral position relative to said second light source and said second light receiver, said first curtain assuming its said first neutral position when said second curtain assumes its said second neutral position.

18. Sensor apparatus according to claim 17, wherein when said first and second curtains move in said first direction from said first and second neutral positions, respectively, the amount of light received by said first light receiver from said first light source increases, while the amount of light received by said second light receiver from said second light source decreases, and vice versa.

19. Sensor apparatus according to claim 18, wherein said third curtain is positionable in a third neutral position relative to said third light source and said third light receiver, and wherein said fourth curtain is positionable in a fourth neutral position relative to said fourth light source and said fourth light receiver, said third curtain assuming its said third neutral position when said fourth curtain assumes its said fourth neutral position.

20. Sensor apparatus according to claim 19, wherein when said third and fourth curtains move in said second direction from said third and fourth neutral positions, respectively, the amount of light received by said third light receiver from said third light source increases, while the amount of light received by said fourth light receiver from said fourth light source decreases, and vice versa.

21. Sensor apparatus according to claim 20, wherein said sensor apparatus is combined with an outsole of footwear.

22. Sensor apparatus according to claim 21, wherein said sensor apparatus measures ground reaction forces acting on the lower extremity of an individual wearing said footwear.

23. Sensor apparatus according to claim 22, wherein said sensor apparatus measures biaxial ground reaction forces.

24. Sensor apparatus according to claim 10, wherein said third sensor unit is independent of said first and second sensor units, and wherein said fourth sensor unit is independent of said first and second sensor units.

25. Footwear retrofitted with sensor apparatus adapted to measure shear ground forces, said sensor apparatus being located in an outsole of said footwear and comprising:
   a first light source;
   a first light receiver located in a fixed position relative to said first light source and configured to receive light emitted from said first light source, wherein said first light source and said first light receiver constitute a first sensor unit;
   a first curtain movably positioned between said first light source and said first light receiver, said first curtain being movable relative to said first light source and said first light receiver so as to adjust the amount of light received by said first light receiver from said first light source;
   a second light source;
   a second light receiver located in a fixed position relative to said second light source and configured to receive light emitted from said second light source, wherein said second light source and said second light receiver constitute a second sensor unit that is independent of said first sensor unit; and
   a second curtain movably positioned between said second light source and said second light receiver, said second curtain being movable relative to said second light source and said second light receiver so as to adjust the amount of light received by said second light receiver from said second light source, said second curtain being movable conjointly with said first curtain in a first direction such that the amount of light received by said first light receiver from said first light source is inversely proportional to the amount of light received by said second light receiver from said second light source.

26. A method of providing existing footwear with the ability to measure ground reaction forces, said method comprising the step of:
   retrofitting an outsole of said existing footwear with sensor apparatus comprising a first light source;
      a first light receiver located in a fixed position relative to said first light source and configured to receive light emitted from said first light source, wherein said first light source and said first light receiver constitute a first sensor unit;
      a first curtain movably positioned between said first light source and said first light receiver, said first curtain being movable relative to said first light source and said first light receiver so as to adjust the amount of light received by said first light receiver from said first light source;
      a second light source;
      a second light receiver located in a fixed position relative to said second light source and configured to receive light emitted from said second light source, wherein said second light source and said second light receiver constitute a second sensor unit that is independent of said first sensor unit; and
      a second curtain movably positioned between said second light source and said second light receiver, said second curtain being movable relative to said second light source and said second light receiver so as to adjust the amount of light received by said second light receiver from said second light source, said second curtain being movable conjointly with said first curtain in a first direction such that the amount of light received by said first light receiver from said first light source is inversely proportional to the amount of light received by said second light receiver from said second light source.

* * * * *